United States Patent [19]

Henne et al.

[11] 4,447,520

[45] May 8, 1984

[54] ACYLPHOSPHINE OXIDES AND THEIR USE

[75] Inventors: Andreas Henne, Ludwigshafen; Anton Hesse, Weinheim; Manfred Jacobi, Frankenthal; Gunnar Schornick, Neuleiningen; Rudolf Vyvial, Ludwigshafen; Klaus Holoch, Bobenheim-Roxheim, all of Fed. Rep. of Germany

[73] Assignee: BASF Aktiengesellschaft, Fed. Rep. of Germany

[21] Appl. No.: 409,555

[22] Filed: Aug. 19, 1982

[30] Foreign Application Priority Data

Aug. 24, 1981 [DE] Fed. Rep. of Germany ....... 3133419

[51] Int. Cl.$^3$ .......................... C07F 9/53; G03C 1/68
[52] U.S. Cl. ..................... 430/281; 430/285; 430/923; 204/159.15; 204/159.23; 260/931
[58] Field of Search ............... 430/281, 285, 913, 914, 430/915, 916, 923, 919; 204/159.15, 159.23; 260/931

[56] References Cited

U.S. PATENT DOCUMENTS

| | | | |
|---|---|---|---|
| 3,715,293 | 2/1973 | Sandner et al. | 204/159.23 |
| 3,801,329 | 4/1974 | Sandner et al. | 430/281 |
| 4,265,723 | 5/1981 | Hesse et al. | 204/159.23 |
| 4,292,152 | 9/1981 | Lechtken et al. | 204/159.15 |
| 4,298,738 | 11/1981 | Lechtken et al. | 546/22 |
| 4,324,744 | 4/1982 | Lechtken et al. | 546/21 |
| 4,385,109 | 5/1983 | Lechtken et al. | 430/281 X |

FOREIGN PATENT DOCUMENTS

| | | |
|---|---|---|
| 7086 | 1/1980 | European Pat. Off. . |
| 7508 | 2/1980 | European Pat. Off. . |
| 2261383 | 6/1973 | Fed. Rep. of Germany . |
| 2830927 | 1/1980 | Fed. Rep. of Germany . |
| 2909994 | 2/1980 | Fed. Rep. of Germany . |
| 3020092 | 12/1981 | Fed. Rep. of Germany . |

*Primary Examiner*—John E. Kittle
*Assistant Examiner*—Cynthia Hamilton
*Attorney, Agent, or Firm*—Keil & Witherspoon

[57] ABSTRACT

Acylphosphine oxides of the general formula

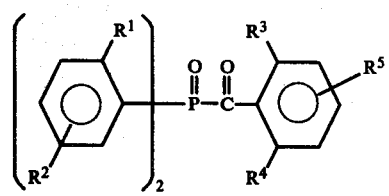

where $R^1$ is methyl or ethyl, $R^2$ is a branched or straight-chain alkyl radical or chlorine, alkoxy or hydrogen, $R^3$ and $R^4$ are identical or different, and are each alkyl, alkoxy, alkylthio or chlorine and $R^5$ is hydrogen, chlorine, alkoxy, alkylthio or alkyl, may be used as photoinitiators in photopolymerizable materials.

6 Claims, No Drawings

ACYLPHOSPHINE OXIDES AND THEIR USE

The present invention relates to novel acylphosphine oxides and their use as photoinitiators in photopolymerizable materials such as coating agents, finishes, printing inks, unsaturated polyester molding materials and recording materials.

German Laid-Open Applications DOS No. 2,830,927 and DOS No. 2,909,994, and European Patent Application Nos. 7,086 and 7,508, have disclosed acylphosphine oxides and their use as photoinitiators. German Laid-Open Application DOS No. 2,909,994 describes acyldiphenylphosphine oxides with the aid of which even pigmented surface coatings can be hardened with UV light. For hardening printing inks and pigmented finishes, there is, however, a need for photoinitiators which permit photohardening of thicker layers than in the case of the compounds described in German Laid-Open Application DOS No. 2,909,994.

We have found, surprisingly, that relatively thick layers of pigmented finishes and of printing inks can be hardened using acyldiphenylphosphine oxides which are methyl-substituted or ethyl-substituted in the 2-position of the phenyl rings bonded to phosphorus. Additional substituents in the phenyl nucleus do not change this effect.

The present invention relates to acylphosphine oxides of the general formula (I)

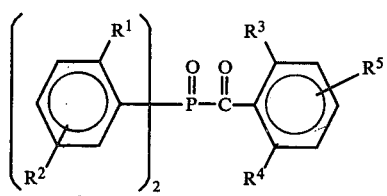

where $R^1$ is methyl or ethyl, $R^2$ is a branched or straight-chain alkyl radical of 1 to 4 carbon atoms, chlorine, alkoxy of 1 to 4 carbon atoms or hydrogen, $R^3$ and $R^4$ are identical or different, and are each alkyl, alkoxy or alkylthio, each of 1 to 4 carbon atoms, or chlorine, and $R^5$ is hydrogen, chlorine, or alkoxy or alkylthio, each of 1 to 6 carbon atoms, or a branched or straight-chain alkyl radical of 1 to 12 carbon atoms.

The present invention furthermore relates to the use of the acylphosphine oxides of the general formula (I) as photoinitiators in photopolymerizable materials, for example for coating agents, finishes and printing inks, and for the production of plastic moldings based on unsaturated polyester resins, where relevant in combination with secondary or tertiary amines, other photoinitiators, or thermal polymerization initiators.

The phenyl ring substituted by $R^1$ and $R^2$ is preferably a 2-methylphenyl or 2,5-dimethylphenyl radical, and that substituted by $R^3$, $R^4$ and $R^5$ is preferably a 2,6-dimethylphenyl, 2,4,6-trimethylphenyl, 2,3,6-trimethylphenyl, 2,6-dimethoxyphenyl, 2,6-dichlorophenyl, 2,6-bis-(methylthio)-phenyl, 2,6-dimethyl-4-tert.-butylphenyl or 2,6-dimethyl-4-octylphenyl radical.

Examples of the novel compounds are:
2,4,6-trimethylbenzoyl-bis-(o-tolyl)-phosphine oxide,
2,6-dimethoxybenzoyl-bis-(o-tolyl)-phosphine oxide,
2,6-dichlorobenzoyl-bis-(o-tolyl)-phosphine oxide,
2,6-dimethyl-4-tert.-butyl-bis-(o-tolyl)-phosphine oxide,
2,6-dimethyl-4-octyl-bis-(o-tolyl)-phosphine oxide,
2,4,6-trimethylbenzoyl-bis-(2,5-dimethylphenyl)-phosphine oxide,
2,6-dimethoxybenzoyl-bis-(2,5-dimethylphenyl)-phosphine oxide,
2,4,6-trimethylbenzoyl-bis-(2,3-dimethylphenyl)-phosphine oxide,
2,6-dichlorobenzoyl-bis-(2,5-dimethylphenyl)-phosphine oxide and
2,6-dimethyl-4-tert.-butyl-bis-(2,5-dimethylphenyl)-phosphine oxide.

The novel substances may be prepared in a manner similar to that described in German Laid-Open Application DOS No. 2,909,994, and the bis-(o-alkylphenyl)alkoxyphosphines required for this purpose may be prepared as described in, for example, German Patent Application No. P 31 02 344.4.

The acylphosphine oxides according to the invention are very reactive as photoinitiators for photopolymerizable monomers having one or more C—C multiple bonds, and mixtures thereof with one another and with conventional additives, and are particularly suitable as photoinitiators in photopolymerizable materials for coatings, finishes, printing inks and recording materials. They are far superior to the conventional photoinitiators, eg. benzil dimethyl ketal, which is disclosed in German Published Application DAS No. 2,261,383, in respect of yellowing of the resulting finishes and coatings. Using the novel compounds, thicker pigmented surface coatings may be hardened than in the case of the acylphosphine oxides described in German Laid-Open Application DOS No. 2,909,994.

The novel commpounds are also very advantageous as photoinitiators for photohardening styrene/polyester resins, which may contain glass fibers and other assistants.

Suitable photopolymerizable monomers are the conventional compounds and substances having polymerizable C—C double bonds which are activated by, for example, aryl, carbonyl, amino, amide, amido, ester, carboxyl or cyanide groups, halogen atoms or additional C—C double or triple bonds, for example vinyl ethers and vinyl esters of 3 to 10, preferably 4 to 8, carbon atoms, vinylaromatics, eg. styrene and vinyltoluene, acrylic and methacrylic acid and esters thereof with monohydric and polyhydric alcohols of not more than 20, preferably 1 to 8, carbon atoms, eg. methyl methacrylate, 2-hydroxyethyl acrylate, 2-hydroxyethyl methacrylate, butane-1,4-diol diacrylate and hexane-1,6-diol diacrylate, nitriles and amides of acrylic and methacrylic acid, maleates and fumarates of alcohols of 1 to 20, preferably 1 to 8, carbon atoms, eg. diethyl fumarate, N-vinyl compounds, eg. N-vinylpyrrolidone, N-vinylcaprolactam and N-vinylcarbazole, and allyl esters, eg. diallyl phthalate.

Examples of suitable photopolymerizable compounds of relatively high molecular weight are unsaturated polyesters prepared from α,β-unsaturated dicarboxylic acids, eg. maleic, fumaric or itaconic acid, mixed if desired, with saturated or aromatic dicarboxylic acids, eg. adipic, phthalic or terephthalic acid, by reacting these acids with alkanediols, eg. ethylene glycol, propylene glycol, butanediol, neopentyl glycol or oxyalkylated bisphenol A; epoxide acrylates prepared from acrylic or methacrylic acid and aromatic or aliphatic diglycidyl ethers, and urethane acrylates, for example prepared from hydroxyalkyl acrylates and polyisocyanates, and polyester acrylates, for example prepared from hydroxyl-containing saturated polyesters and acrylic or methacrylic acid.

Saturated and/or unsaturated polymers and other additives, eg. thermal polymerization inhibitors, paraffin, pigments, dyes, peroxides, leveling agents, fillers, glass fibers, and stabilizers against thermal or photochemical degradation, may be added to the photopolymerizable compounds in a conventional manner, the type and amount of additive depending on the particular end use.

The composition of the photopolymerizable compounds for a particular end use, and mixtures of these compounds with the above additives, are familar to a skilled worker.

The acylphosphine oxides according to the invention are employed in these mixtures in general in a concentration of from 0.01 to 15, preferably from 0.05 to 5, % by weight, based on the photopolymerizable material. If desired, they may be combined with accelerators which eliminate the inhibitory effect of atmospheric oxygen on the photopolymerization.

Examples of such accelerators or synergistic agents are secondary and/or tertiary amines, eg. methyldiethanolamine, dimethylethanolamine, triethylamine, triethanolamine, ethyl p-dimethylaminobenzoate, benzyldimethylamine, dimethylaminoethyl acrylate, N-phenylglycine and N-methyl-N-phenylglycine, and similar compounds which are known to those skilled in the art. Hardening can also be accelerated by using aliphatic and aromatic halides, eg. 2-chloromethylnaphthalene and 1-chloro-2-chloromethylnaphthalene, and, where relevant, agents which form free radicals and are generally used as thermal polymerization initiators, eg. peroxides, azo compounds and compounds with a labile carbon-carbon bond, these being added in amounts of not more than 15% by weight, based on the photopolymerizable material, and being known to a skilled worker.

The acylphosphine oxides can furthermore be used in the presence or absence of the above synergistic agents and accelerators, or in combination with other photoinitiators for photohardening coatings, finishes and printing inks, for photosensitive recording materials, eg. photopolymerizable printing plates, and in styrene-/polyester resins. Examples of such photoinitiators are aromatic ketones, eg. benzil ketals, benzoin ethers, benzoin esters, $C_1$-$C_3$-alkyl-, chloro- or chloromethyl-substituted thioxanthones, the acylphosphines described in German Patent Application No. P 30 20 092.1, the acylphosphine oxides and acylphosphinic acid esters disclosed in German Laid-Open Applications DOS No. 2,830,927 and DOS No. 2,909,994, and aromatic disulfides and naphthalenesulfonyl chlorides, as well as any other suitable compounds known to a skilled worker.

Sources of radiation which preferentially emit light in the absorption range of the compounds according to the invention, ie. between 230 and 450 nm, are generally used for triggering the polymerization of the above mixtures. Low-, medium- and high-pressure mercury vapor lamps, superactinic fluorescent tubes and pulsed discharge lamps are particularly suitable. If appropriate, the said lamps may be doped.

A particular advantage of the acylphosphine oxides according to the invention is that they can be used as photoinitiators for photopolymerization with light sources which have a relatively long wavelength and are therefore less dangerous, eg. fluorescent tubes, or for hardening by sunlight.

In the Examples which follow, parts and percentages are by weight, unless stated otherwise. Parts by volume bear the same relation to parts by weight as that of the liter to the kilogram.

Examples of the novel compounds are given in Table 1, but the invention is not restricted to these.

The compounds listed in Table 2 are taken from German Laid-Open Application DOS No. 2,909,994, for comparison.

TABLE 1

| Acylphosphine oxide according to the invention | Melting point | Analysis | | | |
|---|---|---|---|---|---|
| | | | C | H | P |
| 1 (2,4,6-trimethylphenyl-C(O)-P(O)-(2-methylphenyl)$_2$) | 155–159° | calculated | 76.6 | 6.65 | 8.24 |
| | | found | 75.3 | 6.8 | 7.95 |
| 2 (2,4,6-trimethylphenyl-C(O)-P(O)-(2,4-dimethylphenyl)$_2$) | 137–139° | calculated | 77.23 | 7.18 | 7.67 |
| | | found | 77.0 | 7.2 | 7.3 |
| 3 (2,6-dimethoxyphenyl-C(O)-P(O)-(2-methylphenyl)$_2$) | 173–177° | calculated | 70.05 | 5.84 | 7.87 |
| | | found | 68.8 | 5.8 | 7.6 |
| 4 (4-tert-butyl-2-methylphenyl-C(O)-P(O)-(2-methylphenyl)$_2$) | 116–120° | calculated | 77.51 | 7.42 | 7.42 |
| | | found | 77.5 | 7.3 | 7.3 |

TABLE 1-continued

| Acylphosphine oxide according to the invention | Melting point | | Analysis | | |
|---|---|---|---|---|---|
| | | | C | H | P |
| 5 CH₃—⟨tolyl(CH₃)₂⟩—C(O)—P(O)(⟨xylyl(CH₃)₂⟩)₂ | 168–170° | calculated | 77.23 | 7.18 | 7.67 |
| | | found | 77.0 | 7.0 | 7.4 |

TABLE 2

| Comparative compounds from German Laid-Open Application DOS 2,909,994 | Melting point | Boiling point | | Analysis | | |
|---|---|---|---|---|---|---|
| | | | | C | H | P |
| I  CH₃—⟨tolyl(CH₃)₂⟩—C(O)—P(O)(C₆H₅)₂ | 94° | — | calculated | 75.86 | 6.03 | 8.91 |
| | | | found | 75.6 | 6.1 | 8.9 |
| II CH₃—⟨tolyl(CH₃)₂⟩—C(O)—P(O)(C₆H₄—CH₃)₂ | 93–108° | — | calculated | 76.58 | 6.69 | 8.22 |
| | | | found | 76.4 | 6.7 | 8.1 |
| III CH₃—⟨tolyl(CH₃)₂⟩—C(O)—P(O)(C₆H₄—Cl)₂ | 135–136° | — | calculated | 63.32 | 4.59 | 7.42 |
| | | | found | 63.0 | 4.6 | 7.2 |
| IV CH₃—⟨tolyl(CH₃)₂⟩—C(O)—P(O)(C₆H₅)(OCH₂CH₃) | 22–24° | 150–3°/ 0.01 mm | calculated | 68.35 | 6.65 | 9.81 |
| | | | found | 68.1 | 6.6 | 10.5 |
| V CH₃—⟨tolyl(CH₃)₂⟩—C(O)—P(O)(CH₃)(O—CH(CH₃)₂) | <20° | 114°/ 0.1 mm | calculated | 62.68 | 7.84 | 11.57 |
| | | | found | 62.5 | 7.8 | 11.2 |

EXAMPLE 1

Preparation of an acylphosphine oxide 122 parts of bis-(o-tolyl)-methoxyphosphine were added dropwise to 91.5 parts by weight of 2,4,6-trimethylbenzoyl chloride in 100 parts by volume of dioxane, under reflux. Thereafter, the mixture was stirred under reflux for a further 5 hours and then cooled to room temperature, and the product was filtered off and recrystallized from toluene.

Yield: 116.9 parts (62% of theory).

Melting point: 155°–159° C.

Analysis: calculated: C 76.6%, H 6.65%, P 8.24%. found: C 75.3%, H 6.8%, P 7.95%.

EXAMPLE 2

An unsaturated polyester resin was obtained by esterifying 143 parts of tetrahydrophthalic anhydride and 175 parts of maleic anhydride with 260 parts of diethylene glycol, 0.01% of hydroquinone was added to the product, and a 64 percent strength solution of this mixture in styrene was prepared.

For the UV hardening experiments, 20 parts of styrene, 30 parts of titanium dioxide (RN 57) and 1.5 parts of the photoinitiator were added to 100 parts of this solution, and the finish was cast onto a glass plate with the aid of a film-casting apparatus (slot width 100 μm).

The film was dried in air for about one minute, and was then irradiated for 20 seconds with a high-pressure mercury vapor lamp (30 watt/cm arc length, Philips HTQ 7) which was located 15 cm above the object.

The hardening was determined using the König pendulum method (DIN No. 53,147), and the results are summarized in Table 3.

In a 2nd series of experiment, a thicker layer of the above solution was cast onto a glass plate with the aid of a film-casting apparatus (slot width 400 μm), and the film was irradiated as described above.

When hardening was complete, the film was peeled off, and washed with acetone, and its thickness was determined. These measurements are also given in Table 3.

It can be seen from the Table that, compared with the comparative compounds I and IV, compounds 1 and 4 have a substantially superior hardening action in pigmented polyester finishes.

TABLE 3
UV hardening of pigmented unsaturated polyester resins

| Initiator | Konig pendulum hardness (seconds) | Curable coating thickness (μm) |
|---|---|---|
| 1 | 72 | 170 |
| 4 | 70 | 160 |
| I | 63 | 100 |
| IV | 26 | 80 |

EXAMPLE 3

1.5 parts of each of the photoinitiators to be compared were dissolved, in each case, in a mixture comprising 56 parts of a reaction product of bisphenol A diglycidyl ether and acrylic acid, 44 parts of hexanediol diacrylate, 30 parts of titanium dioxide (rutile) and 3 parts of methyldiethanolamine.

The finish was cast onto glass plates with the aid of a film-casting apparatus (slot width 100 μm), and the film was hardened at a belt speed of 5 m/minute, under a high-pressure mercury vapor lamp (100 watt/cm arc length. Original Hanau Q 67 19) which was located 10 cm above the belt.

The hardening was determined by the König pendulum method (DIN No. 53,147), and the results are summarized in Table 4.

In a 2nd series of experiments, the above finishes were cast onto glass plates with the aid of a film-casting apparatus (400 μm), and the films were hardened as described above, but at a belt speed of 10 m/minute.

When hardening was complete, the films were peeled off, and washed with acetone, and their thicknesses were determined. These measurements are also given in Table 4.

TABLE 4

| Initiator | Pendulum hardness (seconds) | Curable coating thickness (μm) |
|---|---|---|
| 1 | 60 | 160 |
| 2 | 59 | 160 |
| I | 55 | 100 |
| II | 55 | 90 |
| III | 56 | 90 |
| IV | 53 | 70 |
| V | wrinkled surface | 20 |

In pigmented finishes, compounds 1 and 2 give hardened layers which are 50–100% thicker than those obtained using comparative compounds I to V.

EXAMPLE 4

To measure the hardening activity, the change in temperature in the unsaturated polyester resin (UP resin) during irradiation with UV light was recorded by immersing a thermocouple, which was coated with a layer of wax and connected to a temperature recorder (®Tastotherm Script 3 N, standard thermocouple T 300 from Deutschen Gulton GmbH), in a tinplate lid which was filled with 10 g of UP resin and had a diameter of 5 cm (thickness of the UP resin: 4.8 mm). The lid was embedded in rigid polyurethane foam in order to avoid heat losses during irradiation with UV light. The radiation source was a UV field comprising 5 fluorescent tubes (TLAK 40 W/05, Philips) arranged side-by-side at a distance of 8.5 cm from the surface of the UP resin.

The hardening time $ht_{25°C\text{-}T_{max}}$ and the maximum hardening temperature $T_{max}$ reached were obtained as characteristic parameters of the hardening activity from the temperature/time curves recorded. The hardening time was the time taken for the temperature of the sample to rise from 25° C. to $T_{max}$.

The polyester resin with which the Examples and Comparative Examples were carried out was a 65 percent strength styrene solution of an unsaturated polyester obtained from maleic acid, o-phthalic acid, ethylene glycol and propylene 1,2-glycol in the molar ratio 1:2:2.3:0.70, and having an acid number of 50, the solution being stabilized by 0.01% of hydroquinone.

TABLE 5
Hardening activity of various compounds

| | Hardening activity | |
|---|---|---|
| Compound | $ht_{25°C\text{-}T_{max}}$ | $T_{max}$ (°C) |
| I | 4 minutes 45 seconds | 125 |
| II | 4 minutes 38 seconds | 101 |
| III | 4 minutes 53 seconds | 103 |
| IV | 7 minutes 08 seconds | 112 |
| V | 8 minutes 30 seconds | 103 |
| 1 | 4 minutes 23 seconds | 122 |
| 2 | 5 minutes 00 seconds | 121 |
| 3 | 5 minutes 38 seconds | 108 |

EXAMPLE 5

3 parts of photoinitiator were dissolved in a binder comprising 65 parts of a reaction product of bisphenol A glycidyl ether and acrylic acid, and 35 parts of hexane-1,6-diol diacrylate. The finished mixture was knife-coated onto glass plates to give a 60 μm thick layer, and the plates were then passed under a high-pressure mercury vapor lamp (power: 80 W/cm of arc length), at a distance of 10 cm. The reactivity is quoted as the maximum possible conveyor belt speed at which a coating which is sufficiently hardened not to be scratched by a fingernail can still be obtained. The results are summarized in Table 6.

EXAMPLE 6

3% of methyldiethanolamine was added to a finish prepared as described in Example 5. As in that Example, the finish was then knife-coated onto glass plates and the plates were exposed. According to the results, which are summarized in Table 6, the speed at which the compounds according to the invention effect hardening can be increased by adding an amine accelerator.

TABLE 6

| | Maximum conveyor belt speed in m/minute | | |
|---|---|---|---|
| Photo-initiator | in air | under an inert gas | in air, with the addition of 3% of methyldiethanol-amine |
| 1 | 12 | 150 | 53 |
| 2 | 15 | 150 | 55 |
| 3 | 15 | 140 | 53 |

We claim:

1. An acylphosphine oxide which may be used as a photoinitiator and is of the formula (I)

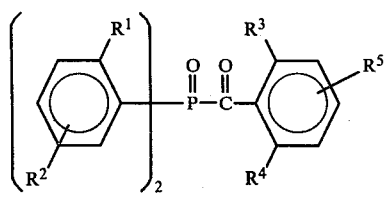 (I)

where R¹ is methyl, R² is a branched or straight-chain alkyl radical of 1 to 4 carbon atoms, chlorine, alkoxy of 1 to 4 carbon atoms or hydrogen, R³ and R⁴ are identical or different, and are each alkyl, alkoxy or alkylthio, each of 1 to 4 carbon atoms, or chlorine, and R⁵ is hydrogen, chlorine, or alkoxy or alkylthio, each of 1 to 6 carbon atoms, or a branched or straight-chain alkyl radical of 1 to 12 carbon atoms.

2. An acylphosphine compound as defined in claim 1, wherein the phenyl radical substituted by R¹ and R² is 2-methylphenyl or 2,5-dimethylphenyl.

3. An acylphosphine compound as defined in claim 1, wherein the phenyl radical substituted by R³, R⁴ and R⁵ is 2,5-dimethylphenyl, 2,4,6-trimethylphenyl, 2,3,6-trimethylphenyl, 2,6-dimethoxyphenyl, 2,6-dichlorophenyl, 2,6-bis-(methylthio)-phenyl, 2,6-dimethyl-4-tert.-butylphenyl or 2,6-dimethyl-4-octylphenyl.

4. A photopolymerizable composition which comprises at least one photopolymerizable monomer having one or more C—C multiple bonds and, as a photoinitiator, an acylphosphine oxide of the formula I as defined in claim 1.

5. A photopolymerizable composition which comprises at least one photopolymerizable monomer having one or more C—C multiple bonds and, as a photoinitiator, an acylphosphine oxide of the formula I as defined in claim 2.

6. A photopolymerizable composition which comprises at least one photopolymerizable monomer having one or more C—C multiple bonds and, as a photoinitiator, an acylphosphine oxide of the formula I as defined in claim 3.

* * * * *